United States Patent [19]

Diamond

[11] Patent Number: 4,757,825

[45] Date of Patent: Jul. 19, 1988

[54] CARDIO-PULMONARY ACTIVITY MONITOR

[75] Inventor: Donald A. Diamond, Bradenton, Fla.

[73] Assignee: Diamond Research Group, Inc., Bradonton, Fla.

[21] Appl. No.: 794,492

[22] Filed: Oct. 31, 1985

[51] Int. Cl.$^4$ ................................................ A61B 5/08
[52] U.S. Cl. ..................................... 128/722; 128/782; 340/575
[58] Field of Search ............... 128/716, 721–723, 128/714, 670–671, 774, 782; 340/573, 575

[56] References Cited

U.S. PATENT DOCUMENTS

| Re. 32,180 | 6/1986 | Lewiner et al. | 128/782 X |
| 2,614,144 | 10/1952 | Howatt | 128/721 X |
| 4,169,462 | 10/1979 | Strubé | 128/721 |
| 4,289,142 | 9/1981 | Kearns | 128/716 |
| 4,320,766 | 3/1982 | Alihanka et al. | 128/722 X |
| 4,381,788 | 5/1983 | Douglas | 128/722 |
| 4,387,722 | 6/1983 | Kearns | 128/716 |
| 4,438,771 | 3/1984 | Friesen et al. | 128/671 |
| 4,509,527 | 4/1985 | Fraden | 128/774 X |

FOREIGN PATENT DOCUMENTS

| 2527475 | 12/1976 | Fed. Rep. of Germany | 128/671 |
| 2829269 | 1/1980 | Fed. Rep. of Germany | 128/774 |

Primary Examiner—William E. Kamm
Assistant Examiner—Angela D. Sykes
Attorney, Agent, or Firm—Duckworth, Allen, Dyer & Doppelt

[57] ABSTRACT

A method and apparatus for providing an indication of a cardiopulmonary activity of a person using noninvasive monitoring means and for detecting motion in the area of the apparatus includes an electrostatic charge detector for providing an output signal including signals indicative of motion and cardiopulmonary activity of the person. A detection apparatus is connected to receive the signals and to filter the extraneous noise signals from the signals of interest to provide output signals indicative only of the motion of interest or cardiopulmonary activity of the person. Breathing signals are applied to a comparator which is tripped if breathing occurs at a rate below a predetermined value. Cardiac signals are applied to a circuit which adjusts the trip level for the breathing rate if the cardiac rate declines to a level suggestive of bradycardia without breathing rate increases. The filtering circuit for the signal supplied by the charge detector incorporates a dual integrator operating as a frequency selective charged amplifier which is effective to substantially eliminate all signals outside of the range of about 0.1 to 15 Hz.

15 Claims, 2 Drawing Sheets

CARDIO-PULMONARY ACTIVITY MONITOR

BACKGROUND OF THE INVENTION

The present invention relates to a method and apparatus for motion monitoring and is particularly described in an embodiment for detecting episodes of apnea in infants.

Research into the problem of infant crib deaths or sudden infant death syndrome (SIDS) in which infants have died during sleep have generally indicated that a significant percentage of infants up to the age of about one year may have problems in the central nervous system reflex such that, during sleep, respiration may cease, a condition referred to as apnea. In most instances, the infant will begin breathing again spontaneously. However, if the duration of an apnea episode is excessive, irreversible cerebral damage may be sustained and, in some cases, death occurs. Clinical procedures have been devised for determining which infants are susceptible to onsets of apnea but are relatively inaccurate.

When an infant is diagnosed as being susceptible to an apnea episode, it is necessary that some method be provided for monitoring the cardio-pulmonary activity of the infant during sleep so that the onset of an episode may be detected quickly and in such a manner that assistance may be provided to the infant to restart breathing. Various types of monitoring devices have been developed for detecting apnea episodes. Notable among these is that disclosed in U.S. Pat. No. 4,474,185 issued Oct. 2, 1984 to the inventor of the present invention. That patent discloses a motion monitor in which very small variations in dielectric constant are measured and used with appropriate timing circuits to provide an alarm when cessation of motion is noted for a predetermined period. Such motion is generally caused by breathing of the patient being monitored, such breathing being associated with motion of the chest and diaphragm. The monitor disclosed therein is essentially a pad which may be placed over a crib mattress or the like and upon which the infant or other patient may lie. In its basic form, the pad includes a plastic film having a zig zag like pattern formed on one surface thereof from a thin metallic foil thereby forming an electrode. An electrostatic shield is formed from a solid sheet of metallic foil which may be bonded to another surface of the first plastic sheet or may be bonded to a second plastic sheet which is then overlayed over the zig zag foil pattern of the first sheet. In either case, the resultant monitoring device appears as a pair of spaced conductive layers separated by an insulating layer.

In order to detect the change in dielectric constant caused by the motion of an infant or other patient adjacent the electrode, the electrostatic shield is connected to an output of a voltage follower, the input of which is connected to the electrode. An oscillator producing a 50 Khz output wave form is provided, and is earth grounded, such that the oscillator pumps earth ground with respect to an internal or floating circuit common such that any moving object between the active electrode and earth ground will act as a modulating dielectric and will change the amplitude of the 50 Khz carrier signal applied. A disadvantage of this system is that the monitor pad must be isolated from earth ground and the system requires a 50 Khz oscillator to generate the carrier signal by pumping earth ground.

A related type of arrangement is disclosed in U.S. Pat. No. 4,438,771 issued Mar. 27, 1984. The device of the latter patent includes a passive charge variation conductive pad spaced from the body which is being monitored and in which a potential is induced by movement of the body, such as, e.g., from the respiratory function or the cardiac function. The induced potential is amplified in order to produce a voltage output representative of movement of the body or change in capacitance or charge distribution on the conductive pad. It is proposed in this patent that movement of a body results in a movement of charge on the body which movement of charge induces a potential in the conductive material of the pad. It is also proposed that each human body or animal body contains a net or at least an accumulation of charge and that motion of the body results in movement of the charge. Although this latter patent uses the same or a very similar type of capacitance probe approach to many of the prior art patents, as distinguished from the single electrode monitor of applicant's U.S. Pat. No. 4,474,185, the system proposed in U.S. Pat. No. 4,438,771 has been found not to be a practical system. In particular, tests have shown that the system of U.S. Pat. No. 4,438,771 is sensitive to electromagnetic interference and may consequently fail to alarm for all apnea episodes. Such interference may comprise, for example, AM and FM radio signals, 60 cycle power line interference and many other high frequency signals generated by, for example, ignition systems of automobiles.

SUMMARY OF THE INVENTION

The present invention utilizes a motion monitor of the type disclosed in Applicant's prior U.S. Pat. Nos. 4,474,185 and 3,973,208, the disclosure of both patents being hereby incorporated by reference. The present invention avoids the necessity of having to pump earth ground by incorporating unique circuitry capable of detecting cardiopulmonary activity even though signals representative of such activity are completely immersed in other noise. Furthermore, it should be noted that applicant's present invention does not require contact between an infant or patient being monitored and the motion monitor. The monitor may be separated from the patient by several layers of material such as, for example, a foam mattress pad or comforter. Although the prior art has suggested that the ability to detect cardio-pulmonary function is dependent upon a charge on a body, it is applicant's position that the activity is not created by a charge on the body since it has been determined that motion of any kind in the presence of the innovative motion monitor will result in detection of an induced charge. In particular, it has been noted that when a parent or other individual enters the room of a patient being monitored, the system will detect charge created by motion of that individual which detection will completely override the small amount of charge produced by breathing or cardiac function of the actual patient. It is suspected that part of this detection is due to the atmospheric potential gradient, i.e., the electric field throughout the atmosphere which produces a potential gradient at sea level of about 2,000 volts per meter and of about 100 to 200 volts per meter at 6 kilometer altitude. Such information regarding the atmospheric potential gradient may be found in the American Institute of Physics Handbook, 3rd Edition published by McGraw Hill Book Company at chapter five, page 292. Furthermore, motion of inanimate objects are also detectable. For example, an overhead fan rotating at slow speed may create a detectable signal within the frequency range of cardiopulmonary activity.

In applicant's invention, the signals induced on the monitor are coupled to a dual integrater circuit which operates as a frequency selective charge amplifier. The amplifier has a band pass between 0.1 and 15 hz. The integrator includes an active feedback network having a very high DC gain to cause the frequency response roll off below 0.1 hz to be very rapid. Accordingly, the signal developed at the output of the amplifier is representative of the electrodynamic changes created by the low frequency activity of breathing and heartbeat.

In one embodiment, the heartbeat rate is detected by the system and used to vary the set point or trip point at which the system will provide an alarm or indication of an onset of apnea. In general, the system is set to trip if the breathing interval drops below some predetermined value, such as for example, 20 seconds. However, if the patient's heart rate decreases, the breathing may become more rapid and not trip the alarm even though it should be tripped since the patient may be suffering from hypoxia. Accordingly, the system will vary the alarm interval set point as a function of heart rate so that as the heart rate drops, at a worse case condition, an alarm will be sounded if a breath doesn't occur every two seconds.

The system further includes indicators for providing output signals representative of each event such as a breathing event or a cardiac event, and for providing an alarm signal on detection of onset of apnea. Furthermore, there is provided a circuit to enable the system to be initialized and deenergized without triggering an alarm.

DESCRIPTION OF THE DRAWING

For a better understanding of the present invention, reference may be had to the following detailed description taken in conjunction with the accompanying drawing in which.

DETAILED DESCRIPTION OF THE PREFERRED EMBODIMENT

Figure 1:
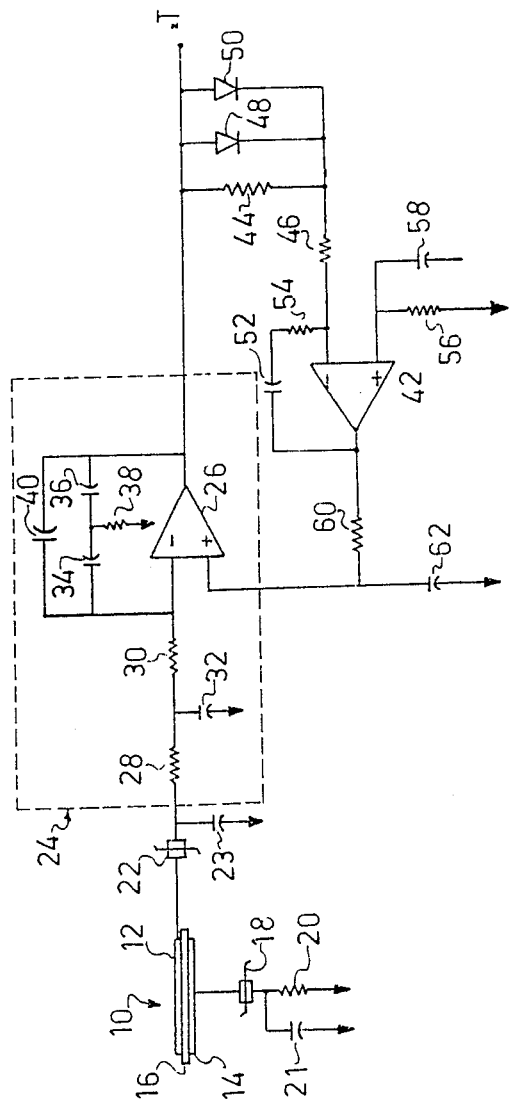
FIG. 1 is a schematic diagram of that portion of the present invention for extracting cardio-pulmonary activity signals from a motion monitor.

The monitoring apparatus and method of the present invention is applicable to many uses for which slight movements of a person are to be detected. However, the invention will be described and explained for use as an apnea monitor and in particular for monitoring the breathing and heart rate, i.e., cardio-pulmonary activity, of an infant while sleeping. Referring now to FIG. 1, a motion monitor charge transducer is shown generally at 10 and is preferably constructed in accordance with the teaching of applicant's prior U.S. Pat. No. 4,474,185. The transducer 10 contains an upper conductive electrode or layer 12 and a lower conductive electrostatic shield or layer 14. An insulative layer 16 separates the upper and lower conductive layers. The lower conductive layer is connected to an earth ground through a ferrite bead 18 and a high impedance resistor 20. A capacitor 21 is connected in parallel with resistor 20. The ferrite bead provides high frequency filtering while the resistor 20 provides a discharge path for accumulated charge on the layer 14. Capacitor 21 decouples RF signals to ground. The active electrode or electrical layer 12 is connected through a second ferrite bead 22 to an input terminal of a frequency selective charge amplifier or dual integrator 24. A capacitor 23 decouples high frequency noise in conjunction with bead 22. The amplifier 24 includes an operational amplifier 26 having an inverting input terminal to which the signal from layer 12 is connected through high impedance input resistors 28 and 30. A capacitor 32 connected between a junction intermediate resistors 28 and 30 and ground operates in conjunction with the resistors 28 and 30 to provide a high frequency filter. The amplifier 26 includes an AC feedback loop connected between an output terminal and the inverting input terminal. The AC feedback loop includes first and second serially connected capacitors 34 and 36 with a resistor 38 connecting the junction intermediate the two capacitors to ground. A ten picofarad capacitor 40 connected in parallel with the series connection of capacitors 34 and 36 prevents high frequency oscillation and is sometimes referred to as a Miller capacitor. It will be appreciated that the circuit as thus far described provides no DC feedback and will thus tend to drift to either the positive or negative rails over time. In order to prevent such drift and to provide for a very fast low frequency roll off, there is included an active feedback network utilizing a second amplifier 42 connected as an operational amplifier for providing DC feedback.

An output terminal of the amplifier 26 is connected through a resistor 44 and resistor 46 to an inverting input terminal of amplifier 42. The resistor 44 is shunted by two reverse parallel connected diodes 48 and 50 which provide a quasilogarithmic amplifier response to reduce large signal saturation of the amplifier 42. The amplifier 42 is also connected as an integrator with a relatively long time constant and as such includes a capacitor 52 connected between its output terminal and inverting input terminal. A resistor 54 connected in series with capacitor 52 sets the AC gain of the amplifier. The non-inverting input terminal of amplifier 42 is connected to earth ground through the parallel combination of a resistor 56 and capacitor 58. An output terminal of amplifier 42 is connected to the noninverting input terminal of amplifier 26 through a coupling resistor 60. An additional capacitor 62 is connected between the noninverting terminal of amplifier 26 and ground to provide suppression of thermal noise generated by the large resistance value resistors. The output signal generated by amplifier 42 is a quasi-analog feedback signal.

The output of the charge amplifier 24 of FIG. 1 at terminal T is primarily the amplified changes in the charge potential on the transducer 10 created by breathing of the person with which the transducer 10 is associated. However, also riding on that signal is a signal of somewhat higher frequency which represents the cardiac rate of the person being monitored. In actual testing, the circuit of FIG. 1 has been found to be extremely practical in stripping out the extraneous noise signals created by 60 hz power lines and radio station signals and other electronic noise generally available in the atmosphere. In constructing the circuit of FIG. 1, the following values were used, where R represents resistor and C indicates capacitor;

| | Ohms |
|---|---|
| $R_{28}$ | 10 M |
| $R_{30}$ | 1 M |
| $R_{38}$ | 1 M |
| $R_{44}$ | 10 M |
| $R_{46}$ | 4.7 M |
| $R_{54}$ | 1 K |
| $R_{56}$ | 10 M |
| $R_{60}$ | 10 M |
| $R_{20}$ | 10 M |
| $C_{21}$ | 0.001 uf |
| $C_{23}$ | 0.001 uf |
| $C_{32}$ | .01 uf |
| $C_{34}$ | .001 uf |
| $C_{36}$ | .001 uf |
| $C_{40}$ | 10 pf |
| $C_{52}$ | 10 uf |
| $C_{58}$ | .01 uf |
| $C_{62}$ | .01 uf |
| $D_{48}$ | 1N914 |
| $D_{50}$ | 1N914 |

The arrangement described in FIG. 1 thus provides amplification of the breathing and cardiac signals developed by a person associated with the transducer 10 and eliminates all of the extraneous signals in which those breathing and cardiac signals are essentially buried. The overall circuit has essentially zero gain for DC and yet has exceedingly high gain between 0.1 hz and 1.5 hz (the fifty per cent attenuation points). The roll off rate at the upper frequency is not as quick as the lower end but does drop off at a rate of about 12 db per octave above about 8 hz. In actual testing, the 60 hz. and 50 hz power signals are inconsequential at the output developed at terminal T. The ferrite beads 18 and 22 in combination with capacitors 21 and 23 essentially eliminate most of the RF and AM radio station interference. Below 0.01 hz., the circuit has approximately 100 second time constant so that the DC gain rapidly drops to zero below 0.01 hz. An important feature of the circuit in FIG. 1 is that it is not necessary to decouple the output of the circuit before applying it to a comparator because the circuit automatically zeros itself and long term offset drift of the amplifier is compensated. In prior art circuits of this nature, the filtering network is such that capacitive coupling is required which then requires fairly sophisticated circuitry for low frequency coupling. Thus, the circuit described above provides the unique features and advantages for detecting the relatively low frequency breathing and cardiac rates of an individual and for excluding extraneous noise signals.

Figure 2:
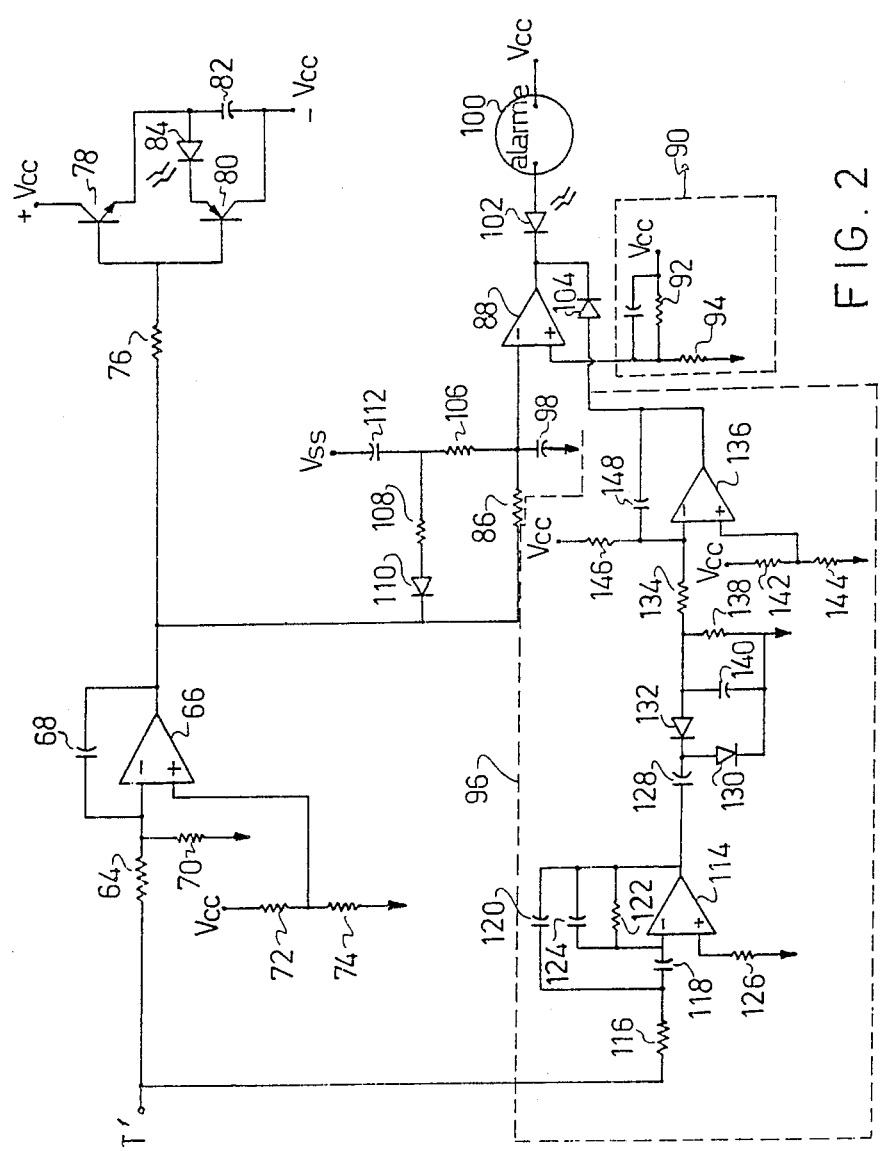
FIG. 2 is a schematic diagram of that portion of the present invention which responds to the signals developed by the circuit of FIG. 1 and also adjusts the system alarm level as a function of cardiac rate.

Referring now to FIG. 2, there is shown a comparator circuit for providing an output signal upon occurrence of each breathing cycle of a patient and an alarm circuit for providing an indication of abnormal breathing. There is also illustrated a circuit for varying the alarm signal level as a function of cardiac activity. The terminal T' corresponds to the terminal T of FIG. 1. The signal developed by the amplifier 24 is coupled through a resistor 64 to an inverting input terminal of a comparator 66. The comparator 66 includes a high frequency shunt capacitor 68 to further filter any high frequency signals on the breathing signal. A bleeder resistor 70 provides a discharge path for capacitor 68. The noninverting input terminal comparator 66 is connected to a voltage divider circuit comprises of first and second resistors 72 and 74 serially connected between a voltage reference $V_{cc}$ and earth ground. The values of resistors 72 and 74 are selected so as to allow the comparator to trip upon receipt of a signal indicative of motion or breathing of a patient being monitored. The output signal developed by the comparator 66 is normally at a positive voltage level but switches to a negative voltage level when the input at the inverting input terminal goes positive, that is, when the patient being monitored either breathes or moves.

The output terminal of comparator 66 is connected through a coupling resistor 76 to an LED indicating circuit comprising first and second transistors 78 and 80. An LED 82 is serially connected between an emitter terminal of transistor 78 and an emitter terminal of transistor 80. A collector terminal of transistor 78 is connected to the positive voltage source $V_{cc}$ and the collector terminal of transistor 80 is connected to a negative of $V_{ss}$. A capacitor 84 is connected between the voltage $V_{ss}$ and one terminal of the LED 82. When the output signal of comparator 66 is a positive level, the transistor 78 is gated into conduction and current through the transistor charges the capacitor 84. When the signal from comparator 66 goes to a negative level, the transistor 78 is gated off and the transistor 80 is gated into conduction. During that time the charge accumulated on capacitor 84 is discharged through the LED 82 and transistor 80 causing the LED 82 to emit light. Thus, the circuit will provide an indication corresponding to each event associated with moving or breathing of the patient being monitored.

The signals developed by the comparator 66 are also coupled to an alarm circuit for energizing a pulsating type of alarm such as the Sonalert (trademark of Mallory) alarm which is a piezoelectric type annunciator. The signal from comparator 66 is coupled through a resistor 86 to an inverting input terminal of a second comparator 88. The noninverting input terminal of comparator 88 is connected to a reference level established in the block 90 by first and second resistors 92 and 94 serially connected between the voltage source $V_{cc}$ and earth ground. It will be apparent that the comparator 88 may be operated from the fixed reference source 90 or may be operated from the variable reference source established in the block 96. Either one or the other of the blocks 90 or 96 may be selected but both would not be used simultaneously. The block 90 is used when the comparison is to be a fixed level and not corrected as a function of cardiac rate. For those instances in which it is desirable to adjust the comparison level as a function of cardiac rate, the circuitry shown in the block 90 is deleted and that circuitry shown in the block 96 is incorporated. Thus, the comparator 88 is set to detect an apnea interval and, as such, the pulses developed by the comparator 66 are accumulated in an integrator comprising the resistor 86 and a capacitor 98. The comparator 88 in conjunction with resistor 86 and capacitor 98 essentially forms an interval timer. The time constant for charging the capacitor 98 is set so that the charge on the capacitor 98 will trip the comparator 88 if breathing events do not occur within a predetermined interval such as, for example, 20 seconds. When the comparator 88 is tripped, i.e., when the voltage on capacitor 98 becomes more positive than the voltage on the noninverting input terminal, the output of comparator 88 will slew to a negative voltage level allowing current to flow through the alarm 100 and a serially connected light emitting diode 102. The LED 102 will glow thereby providing a visual indication of an alarm condition and the alarm 100 will provide an audible indication of an alarm condition. When the output of comparator 88 is negative, a diode 104 connected between the reference voltage source at the noninverting terminal comparator 88 and its output terminal will be forward biased and will act as a latch to prevent the alarm from being turned off until a manual reset has been performed by deenergizing the unit. This action provides a safety circuit to prevent a reset until someone has been notified of the apnea episode.

As was described above, the positive voltage developed by comparator 66 charges the capacitor 98 and when the charge reaches a predetermined value causes the comparator 88 to change states. When a breathing event occurs, the output of comparator 66 goes to a negative value. At this time, the charge on capacitor 98 is removed or discharged. The discharge occurs through resistors 106 and 108 and diode 110. It should be noted that a junction intermediate resistors 106 and 108 is connected through a capacitor 112 to negative voltage source $V_{ss}$. The capacitor 112 provides an initializing current on a restart, i.e., when power is first applied to the system. Without the capacitor 112, the system would automatically go into alarm condition whenever power was applied. Capacitor 112 forces the comparator 88 inverting input to a negative value to allow it to be initialized with a positive output voltage.

Turning now to the circuit indicated in block 96 of FIG. 2, it is seen that the input terminal T' is connected to a band pass filter circuit utilizing an operational amplifier 114. The inverting input terminal of amplifier 114 is connected to terminal T' through a coupling resistor 116 and capacitor 118. A capacitor 120 connected between an output amplifier 114 and the junction intermediate resistor 116 and capacitor 118 operates in conjunction with those latter elements to set the band pass for the amplifier. The resistor 122 connected between the output terminal and the inverting input terminal provides the DC feedback while a capacitor 124 connected in parallel with resistor 122 prevents high frequency oscillations. The noninverting terminal of amp 114 is connected through a resistor 126 to earth ground. The band pass filter is designed to have a center frequency of about 6.8 hz so as to filter out the pulses caused by breathing of the patient being monitored and to pass only those pulses corresponding to the cardiac activity. As mentioned previously, the cardiac activity pulses appear as essentially a sinusoidal wave modulating the breathing signals. The amplified breathing signals may vary in amplitude between 500 millivolts and 2 volts peak-to-peak depending upon the intensity of the breath and the size and orientation of the patient being monitored. The cardiac pulses are in the range of 100 millivolts in amplitude and are superimposed on the pulmonary activity. The signals representative of cardiac activity are coupled through a decoupling capacitor 128 and rectifying circuit comprising diodes 130 and 132 and then through a coupling resistor 134 to an inverting input terminal of a comparator 136. A filter circuit comprising a resistor 138 and parallel connected to capacitor 140 are connected between an anode terminal of diode 132 and earth ground. The filter circuit acts as an integrator with approximately a one second time constant so that a charge can be developed on the capacitor 140 as the cardiac rate of the patient being monitored increases. If the cardiac rate goes below a set value, the output signal developed by the comparator 136 will slew to a lower level which may be a negative value and will allow the comparison between the voltage on capacitor 98 and the voltage developed by the output of comparator 88 to be based on a much lower value thereby causing the comparator to trip at a reduced breathing time interval. The initial value at which the comparator 136 will trip is set by connecting the noninverting terminal of comparator 136 to a junction intermediate first and second resistors 142 and 144 which are connected as a voltage divider between negative voltage source $V_{ss}$ and earth ground. The inverting input terminal of comparator 136 is connected through a resistor 146 to positive voltage source $V_{cc}$ whereby the inverting input terminal is normally held at approximately ground potential. A capacitor 148 connected between the output terminal of comparator 136 and its inverting input terminal provides a high frequency shunt.

Although other values of components could be selected for use in the circuit of FIG. 2, the following is a tabulation of the values used in my preferred embodiment:

|  | Ohms |
| --- | --- |
| $R_{64}$ | 10 k |
| R | 10 M |
| $R_{72}$ | 10 M |
| $R_{74}$ | 100 k |
| $R_{76}$ | 10 k |
| $R_{86}$ | 10 M |
| $R_{92}$ | 1 M |
| $R_{94}$ | 10 M |
| $R_{106}$ | 10 k |
| $R_{10}$ | 47 k |
| $R_{116}$ | 4.7 k |
| $R_{122}$ | 10 M |
| $R_{126}$ | 10 M |
| $R_{138}$ | 10 M |
| $R_{134}$ | 100 k |
| $R_{146}$ | 10 M |
| $R_{142}$ | 10 M |
| $R_{144}$ | 1 M |
| $C_{68}$ | .01 uf |
| $C_{84}$ | 100 uf |
| $C_{112}$ | .01 uf |
| $C_{98}$ | .47 uf |
| $C_{118}$ | .047 uf |
| $C_{120}$ | .22 uf |
| $C_{124}$ | 370 pf |
| $C_{128}$ | .1 uf |
| $C_{140}$ | .1 uf |
| $C_{148}$ | .01 uf |

The operational amplifier and comparator circuits used in the arrangement described in FIG. 1 and FIG. 2 are of a type well known in the art and available from numerous different manufacturers under different numbers. Although the system has been shown using discreet components, it is apparent that the system could be easily implemented using large scale integrated circuits. Furthermore, although the system has been disclosed as a monitor for cardiopulmonary activity, it will be apparent that the system will detect motion of any type within the general area of the transducer, including motion associated with inanimate objects. It should also be noted that the transducer uses only a single electrode and that the layer 14 operates only as an electrostatic shield. Although the circuit has been described in what is presently considered to be a preferred embodiment, it will become apparent to those skilled in the art that many modifications and variations may be utilized without departing from the true scope and spirit of the invention. Accordingly, it is intended that the appended claims be the broadest interpretation commensurate with the scope of the invention.

What is claimed is:

1. Apparatus for monitoring cardiopulmonary activity of an individual and for providing an indication of abnormal activity comprising:
   electrostatic charge collection means for positioning adjacent an individual whose cardiopulmonary activity is to be monitored said collection means having at least first and second spaced layers separated by an electrically insulative layer;
   a dual integrator connected to said collection means for providing an output signal representative of changes in the electrostatic charge on said collection means occurring at a frequency between 0.1 Hz and 15 Hz;
   an amplifier connected in a feedback circuit between an output terminal of said dual integrator and an input terminal thereof, said amplifier having a relatively high gain at frequencies below 0.1 Hz and a relatively low gain at frequencies above 0.1 Hz whereby the output signal of said dual integrator remains substantially at a predetermined value for input signals below 0.1 Hz in frequency; and
   means connected to the output terminal of said dual integrator for providing an indication of the status of the cardiopulmonary activity.

2. The apparatus of claim 1 and including means responsive to a portion of said output signals representative of pulmonary activity for providing an alarm indication when the pulmonary activity rate is less than a set value.

3. The apparatus of claim 2 and including means responsive to a portion of said output signals representative of cardiac activity for changing said set value as a function thereof.

4. The apparatus of claim 3 wherein said means responsive to said cardiac activity signals comprises a bandpass filter having a center frequency of approximately 6.8 Hz.

5. A motion detector of the type including an electrostatic charge collector having an electrically insulated charge collection layer, the detector comprising:
   a frequency selective charge amplifier means connected to the charge collector for providing successive signals each representative of a charge variation on the collector indicative of a motion event, said amplifier means providing said signals in response to events occurring within a predetermined range of time intervals; and
   a frequency selective feedback circuit connected between an output terminal and an input terminal of said amplifier means, said circuit comprising a variable gain apparatus having a relatively high gain at frequencies below a predetermined value whereby the frequency response of said amplifier amplifier falls rapidly below said predetermined value.

6. The detector of claim 5 and including an electrostatic shield substantially co-extensive with the charge collection layer and spaced therefrom by an insulative layer, said shield being connected to an earth ground through a high frequency bypass filter.

7. The detector of claim 6 wherein said amplifier means is a dual integrator having a pass band of about 0.1 to 15 Hz.

8. The detector of claim 7 wherein said predetermined frequency value is approximately 0.1 Hz.

9. The detector of claim 7 wherein said amplifier means is connected to the collection layer through a ferrite bead, and including a capacitor connected between an input terminal of said amplifier means and earth ground whereby high frequency components of signals from the collection layer are filtered by said ferrite bead and capacitor combination.

10. The detector of claim 9 and including means for comparing the time intervals between successive ones of said signals and for generating an output signal when one of the time intervals exceeds a preset interval.

11. The detector of claim 10 wherein said collection layer signals are generated in response to cardiopulmonary activity of a person positioned near the charge collector.

12. The detector of claim 11 and including means for detecting cardiac generated signals representative of heart beat activity independent of signals representing pulmonary activity.

13. The detector of claim 12 and including means responsive to said cardiac signals for varying the preset interval.

14. The detector of claim 13 wherein said means for detecting cardiac signals comprises a bandpass filter.

15. The detector of claim 13 wherein said preset interval varying means comprises an integrator means for developing an analog signal representative of cardiac rate, a comparator means producing a first value signal for comparing said analog signal to a reference signal and for generating a second value signal when said analog signal exceeds said reference signal, said first and second value signals establishing said preset interval having two values.

* * * * *